United States Patent
Gharibian

[11] Patent Number: 5,938,675
[45] Date of Patent: *Aug. 17, 1999

[54] SURGICAL SCALPEL

[75] Inventor: Noel Gharibian, Glendale, Calif.

[73] Assignee: Beckton, Dickinson and Company, Franklin Lakes, N.J.

[*] Notice: This patent is subject to a terminal disclaimer.

[21] Appl. No.: 08/666,734

[22] Filed: Jun. 18, 1996

Related U.S. Application Data

[63] Continuation-in-part of application No. 08/376,065, Jan. 20, 1995, Pat. No. 5,527,329, which is a continuation of application No. 08/163,938, Dec. 8, 1993, abandoned.

[51] Int. Cl.⁶ ..................................................... A61B 17/32
[52] U.S. Cl. ................................. 606/167; 30/2; 30/151; 30/162; 30/335
[58] Field of Search ..................................... 606/166, 167, 606/170, 172, 181, 182, 185; 30/2, 151, 162, 164, 167, 286, 335

[56] References Cited

U.S. PATENT DOCUMENTS

| | | |
|---|---|---|
| D. 327,125 | 6/1992 | Iten . |
| D. 329,699 | 9/1992 | Schutte et al. . |
| D. 330,082 | 10/1992 | Schutte et al. . |
| 2,735,176 | 2/1956 | Costin . |
| 2,885,780 | 5/1959 | Campbell . |
| 2,968,489 | 1/1961 | Doniger . |
| 3,025,598 | 3/1962 | Nissen . |
| 3,657,812 | 4/1972 | Lee . |
| 3,793,726 | 2/1974 | Schrank . |
| 3,905,101 | 9/1975 | Shepherd . |
| 3,906,626 | 9/1975 | Riuli . |
| 4,091,537 | 5/1978 | Stevenson, Jr. . |
| 4,375,218 | 3/1983 | DiGeronimo . |
| 4,414,974 | 11/1983 | Dotson et al. . |
| 4,491,132 | 1/1985 | Aikins . |
| 4,523,379 | 6/1985 | Osterhout et al. . |
| 4,660,287 | 4/1987 | Decker . |
| 4,663,846 | 5/1987 | Takayama . |
| 4,735,202 | 4/1988 | Williams . |
| 4,805,304 | 2/1989 | Knoop . |
| 4,823,457 | 4/1989 | Prochaska . |
| 4,844,070 | 7/1989 | Dee . |
| 4,884,569 | 12/1989 | Fedorov et al. . |
| 4,949,458 | 8/1990 | Davis et al. . |
| 5,055,106 | 10/1991 | Lundgren . |
| 5,071,418 | 12/1991 | Rosenbaum . |
| 5,071,426 | 12/1991 | Dolgin et al. . |
| 5,141,517 | 8/1992 | Shutt . |
| 5,201,748 | 4/1993 | Newman et al. . |
| 5,207,696 | 5/1993 | Matwijcow . |
| 5,250,063 | 10/1993 | Abidin et al. . |
| 5,250,064 | 10/1993 | Schneider . |
| 5,299,357 | 4/1994 | Wonderley et al. . |
| 5,309,641 | 5/1994 | Wonderley et al. . |
| 5,312,429 | 5/1994 | Noack . |

FOREIGN PATENT DOCUMENTS 3722899  1/1989  Germany .

Primary Examiner—Michael Buiz
Assistant Examiner—William Lewis
Attorney, Agent, or Firm—Arthur D. Dawson

[57] ABSTRACT

A surgical scalpel has a retractable sleeve. An elongated handle with a contoured grip portion is releasably attached to a blade holder securing a surgical blade. The blade holder is secured to the handle by a hook and groove assembly and a male to female connection. The sleeve slides between an extended position and a retracted position on the handle and blade holder. The extended position of the sleeve covers the blade thereby protecting operating room personnel. An arch on the sleeve contacts the hook and disengages the hook out of the groove to facilitate removal of the blade holder.

7 Claims, 18 Drawing Sheets

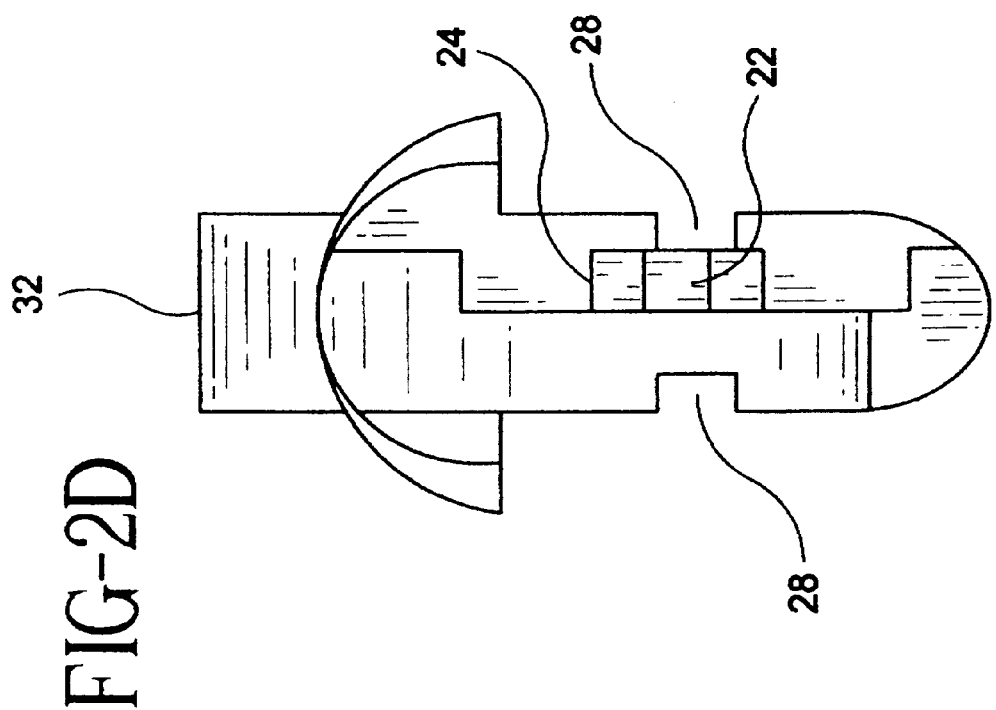
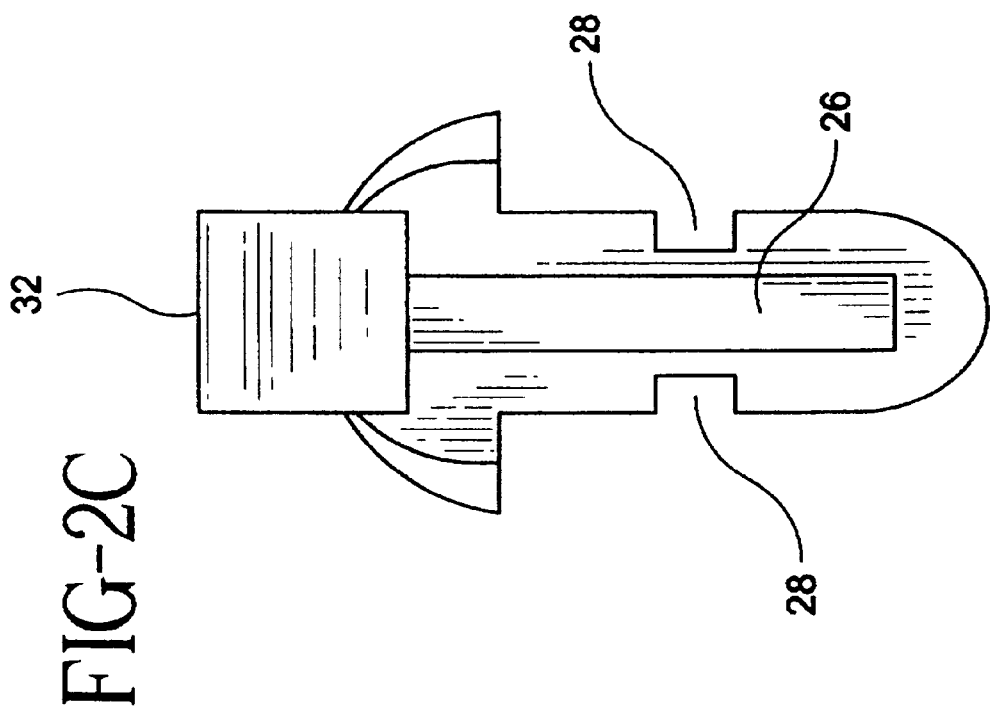

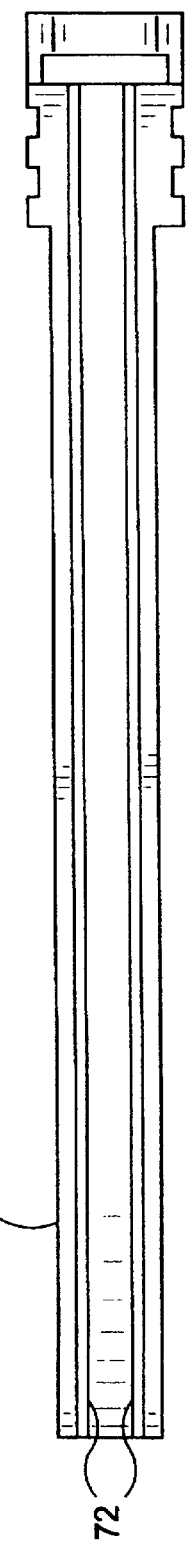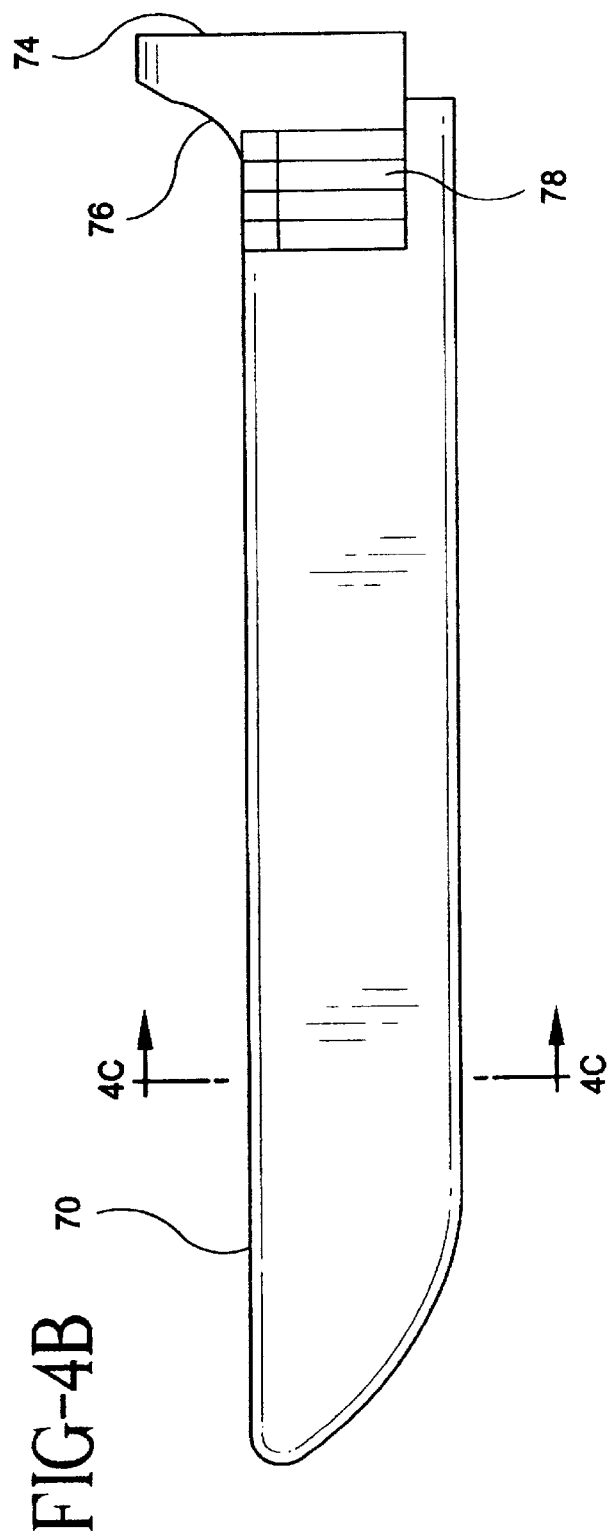
FIG-4A
FIG-4B

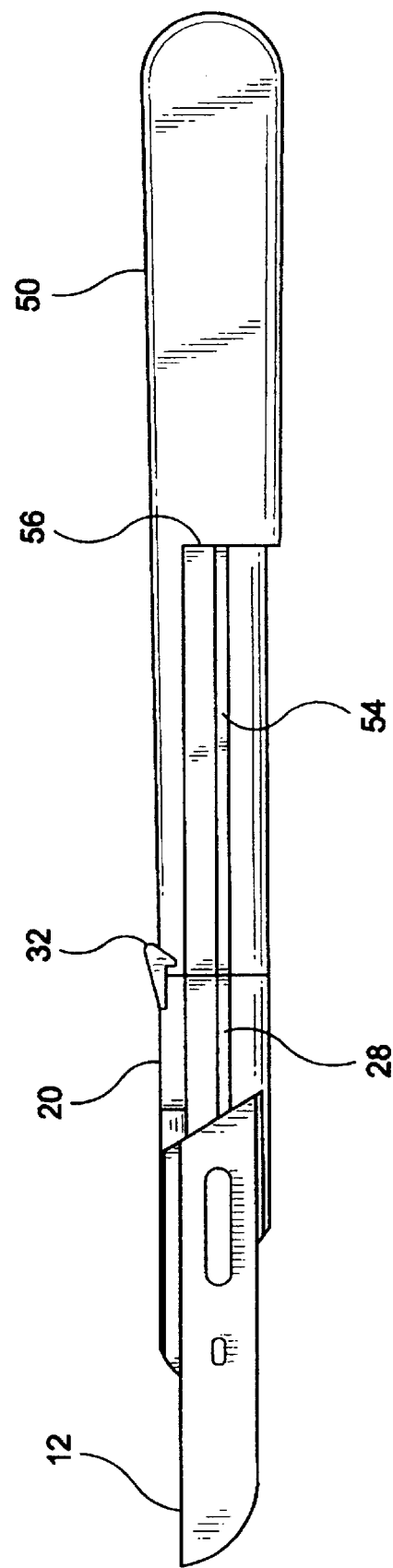

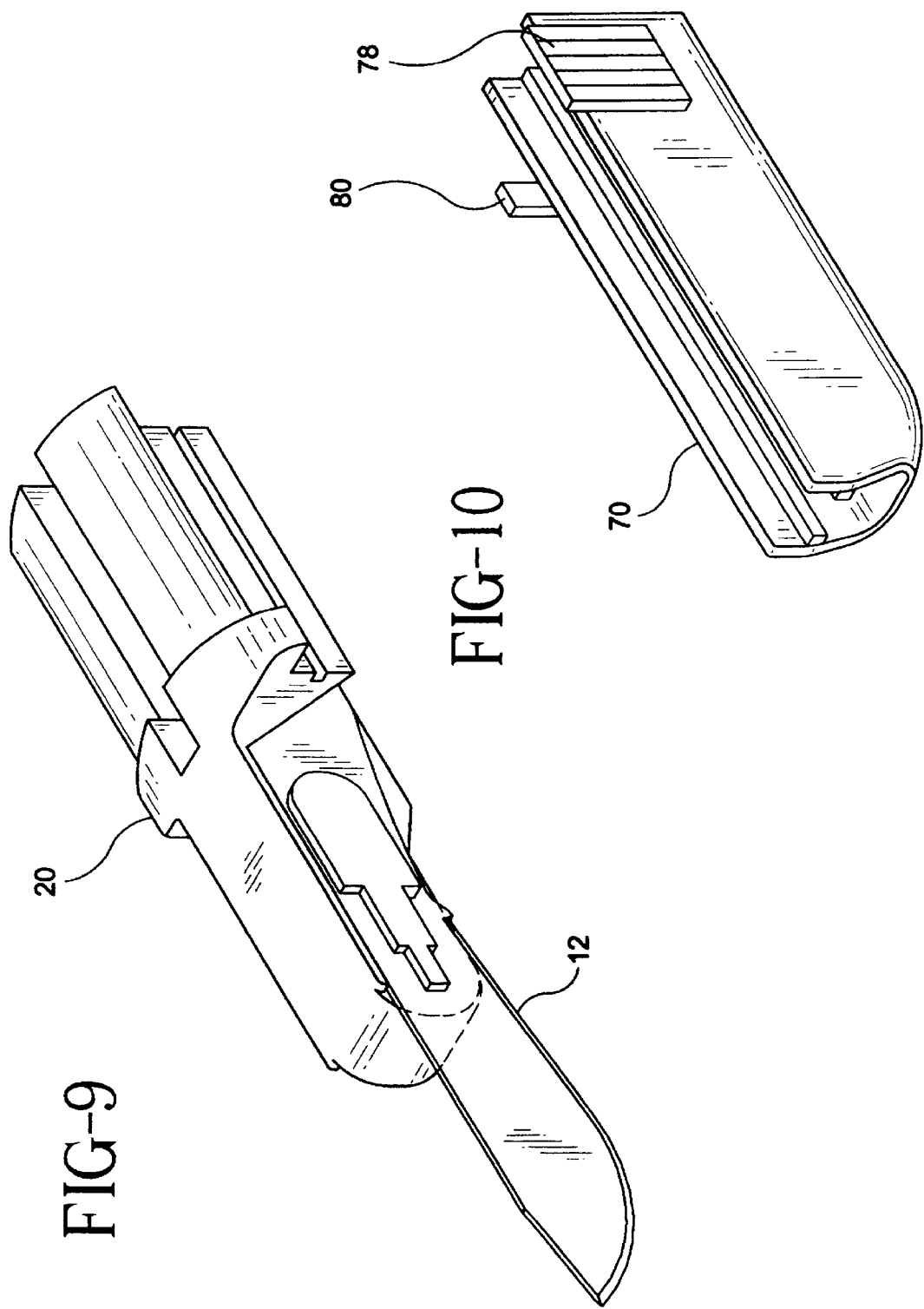

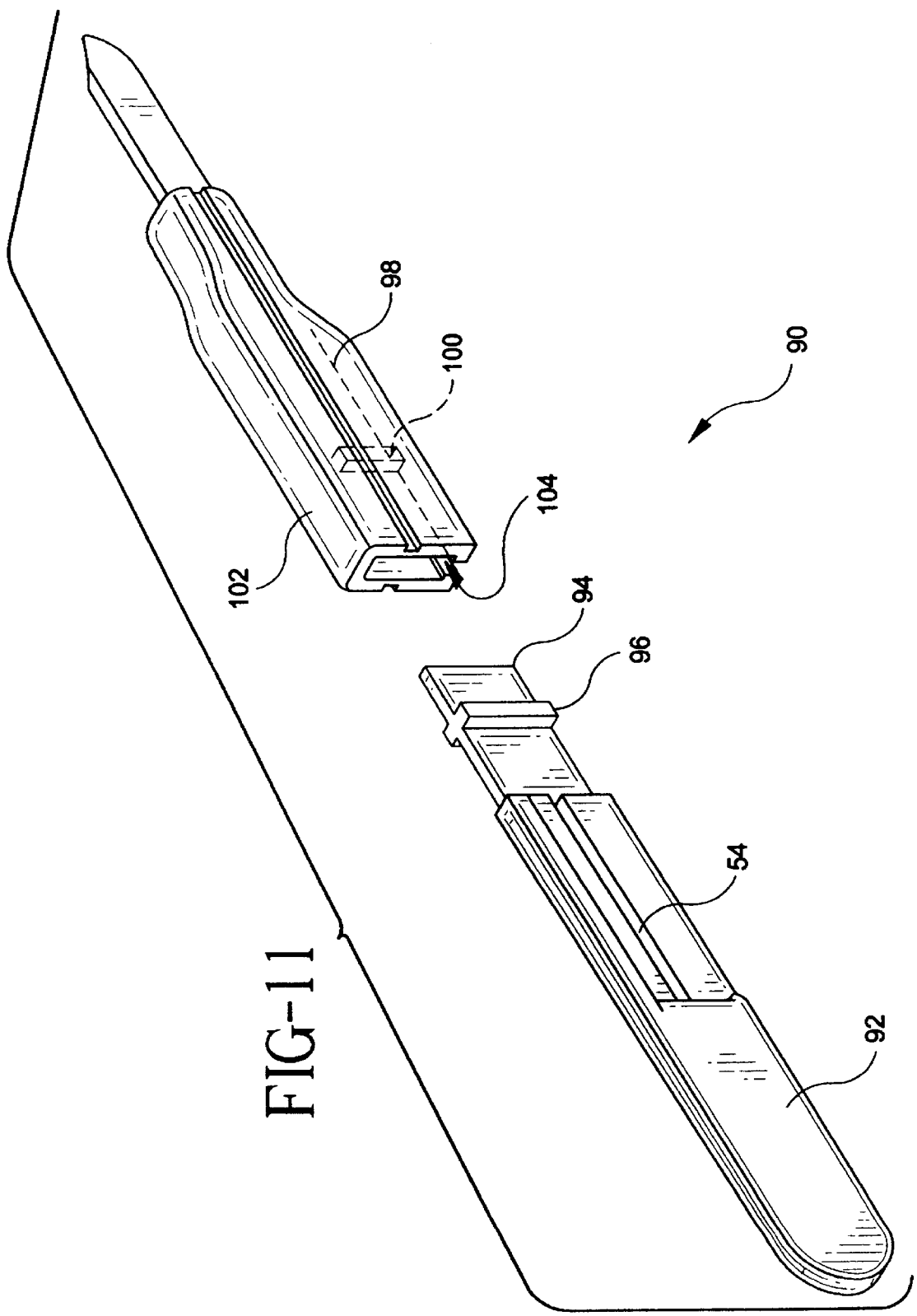

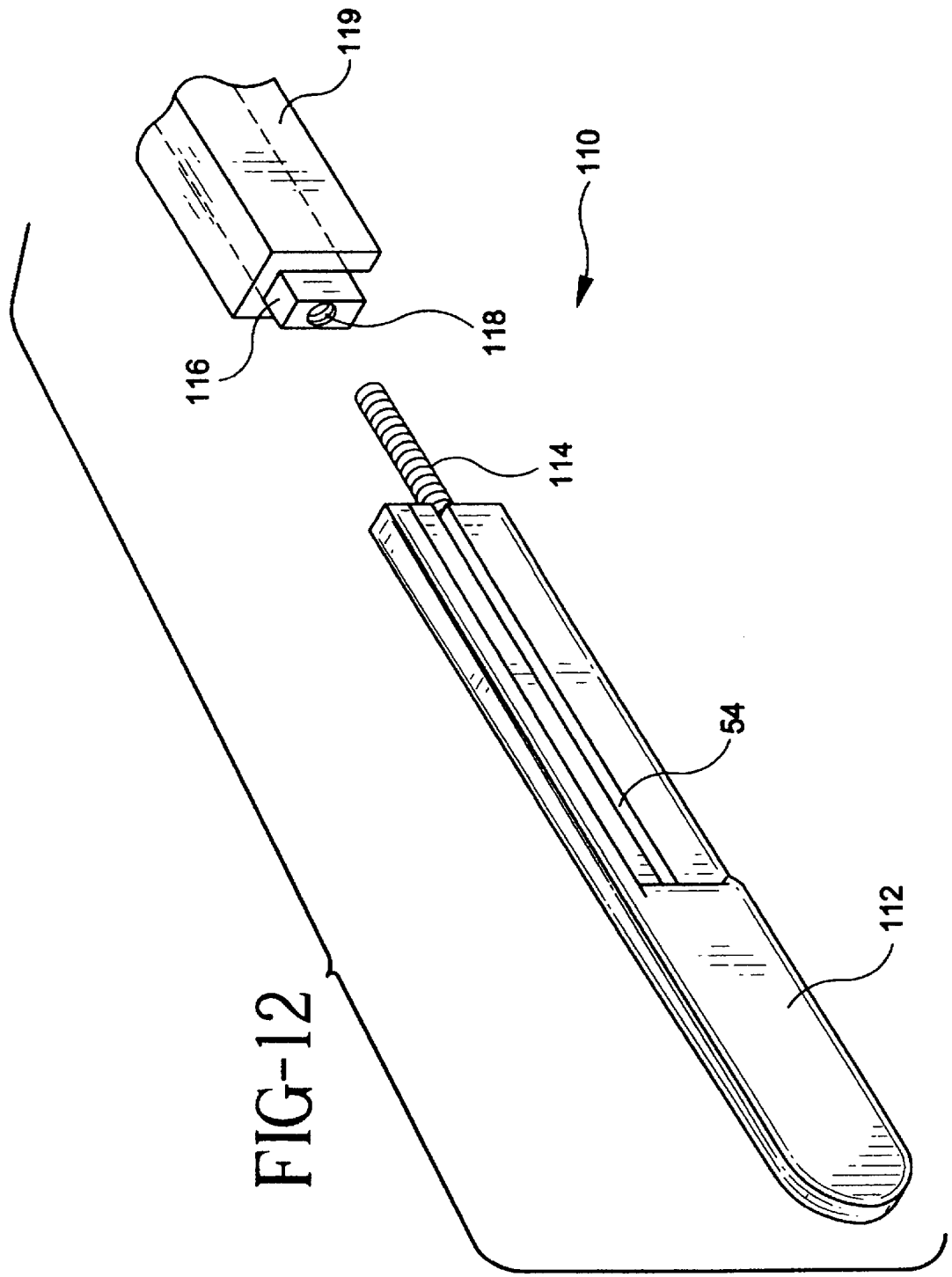

SURGICAL SCALPEL

This application is a Continuation-In-Part of U.S. patent application Ser. No. 08/376,065, filed Jan. 20, 1995, and now U.S. Pat. No. 5,527,329, issuing Jun. 18, 1996, which is a Continuation Application of application Ser. No. 08/163,938, filed on Dec. 8, 1993, abandoned.

BACKGROUND OF THE INVENTION

The field of the invention is surgical cutting instruments. Conventional surgical instruments provide a significant potential for harm to surgeons, nurses and other support personnel. In the operating room, various surgical instruments are quickly passed by hand. The rapid handling of such instruments with exposed sharp edges can lead to accidental cuts or puncture wounds. Surgical gloves may also be inadvertently punctured leading to loss of glove integrity further increasing the risk of infection to a surgeon, nurse or other medical personnel.

Previous attempts to guard against inadvertent cuts or punctures led to the development of retractable blade guards. Some of the earliest versions were simply retractable bladed knives used in various industries outside the medical field. These blade guards generally required two hands to operate, i.e., one hand to manipulate the blade and a second hand to secure the blade guard by turning a threaded screw. Other conventional devices having spring loaded moving parts or tabs that clipped into notches on a hollow tubed sheathing device, were not practical for surgical use because they did not provide a good grip or "feel" for the blade.

SUMMARY OF THE INVENTION

The present invention is directed to an improved scalpel. Preferably, a handle has a male or female end on one end to which a blade holder is attached. A sleeve or cover most desirably slides onto both the handle and the blade holder, preferably by guide flanges that engage channels on both pieces. The surgical blade may be exposed for use by retracting the sleeve. The blade may be covered by manually manipulating the sleeve into an extended position. In a preferred embodiment, the handle is metal and the blade holder is plastic, allowing the natural friction forces to hold them together.

The blade holder and the sleeve may advantageously be removed as a unit and the used blade easily disposed of while covered. The scalpel provides a good feel for or grip on the blade because the blade is secured to the handle. Accordingly, it is an object of the invention to provide an improved scalpel having a blade cover or sheath. Other and further objects and advantages will appear hereinafter to those skilled in the art from the following description and the accompanying drawings.

BRIEF DESCRIPTION OF THE DRAWINGS

In the drawings, wherein similar reference numbers denote similar elements throughout the several views:

FIG. 2c is a back end view of the blade holder showing the hook and the attachment slot;

FIG. 2d is a front end view thereof;

FIG. 4a is a top view of the sleeve;

FIG. 4b is a side elevation view thereof;

FIG. 5c is a side elevation view with the sleeve removed;

FIG. 9 is a perspective view of an alternative embodiment of the blade holder having a female end connection;

FIG. 10 is a perspective view of an alternate embodiment of the sleeve;

FIG. 11 is a perspective view of an alternative embodiment with the blade holder attached to the handle using vertical slots and tabs;

FIG. 12 is an exploded partial perspective view of an alternative embodiment with the blade holder threaded onto the handle;

DETAILED DESCRIPTION OF THE PREFERRED EMBODIMENT

Figure 1:
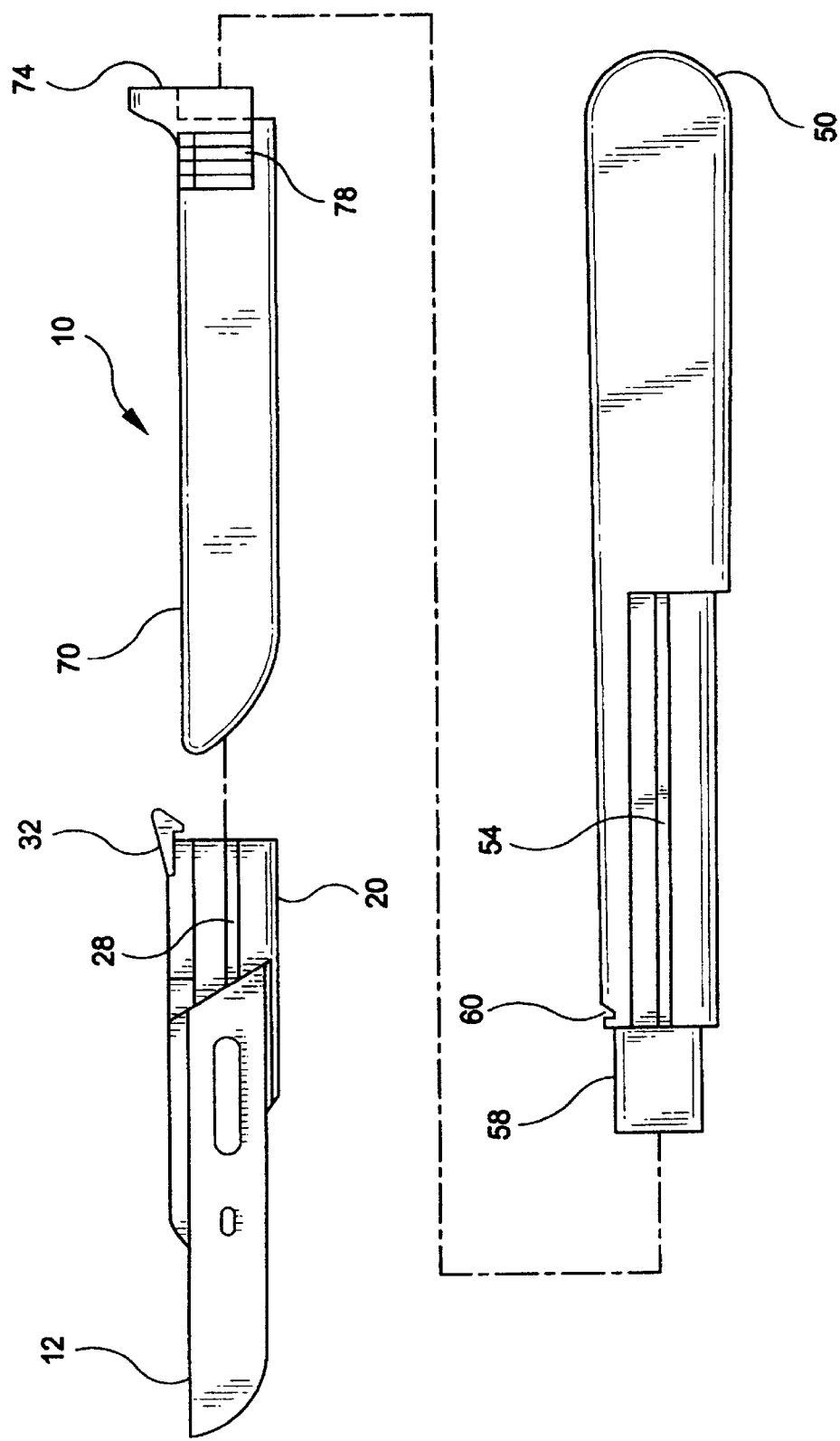
FIG. 1 is an exploded side elevation view of a preferred embodiment of the present scalpel.
Figure 2A:
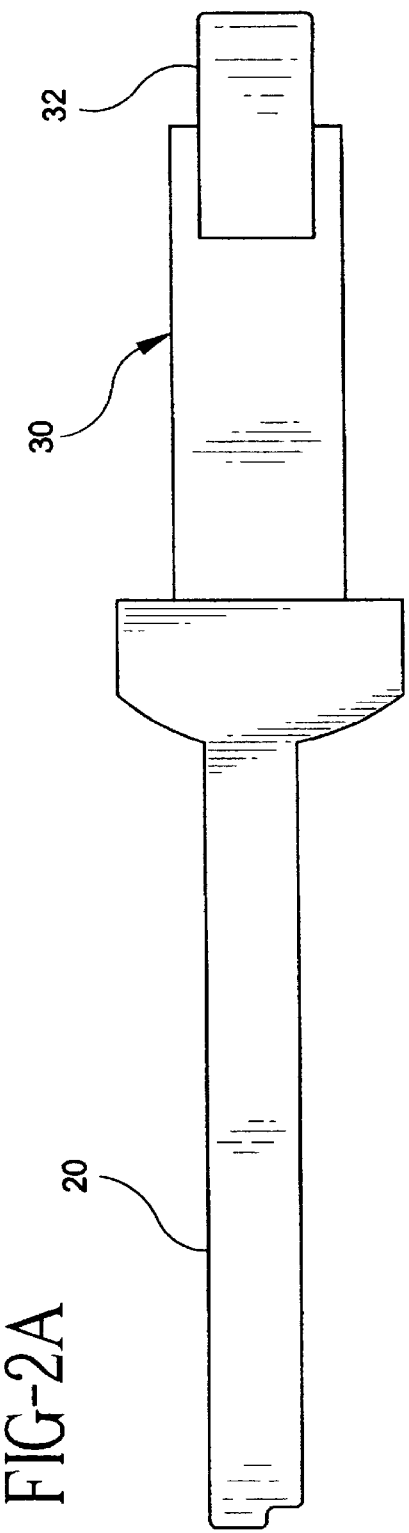
FIG. 2a is a top view of the blade holder.
Figure 2B:
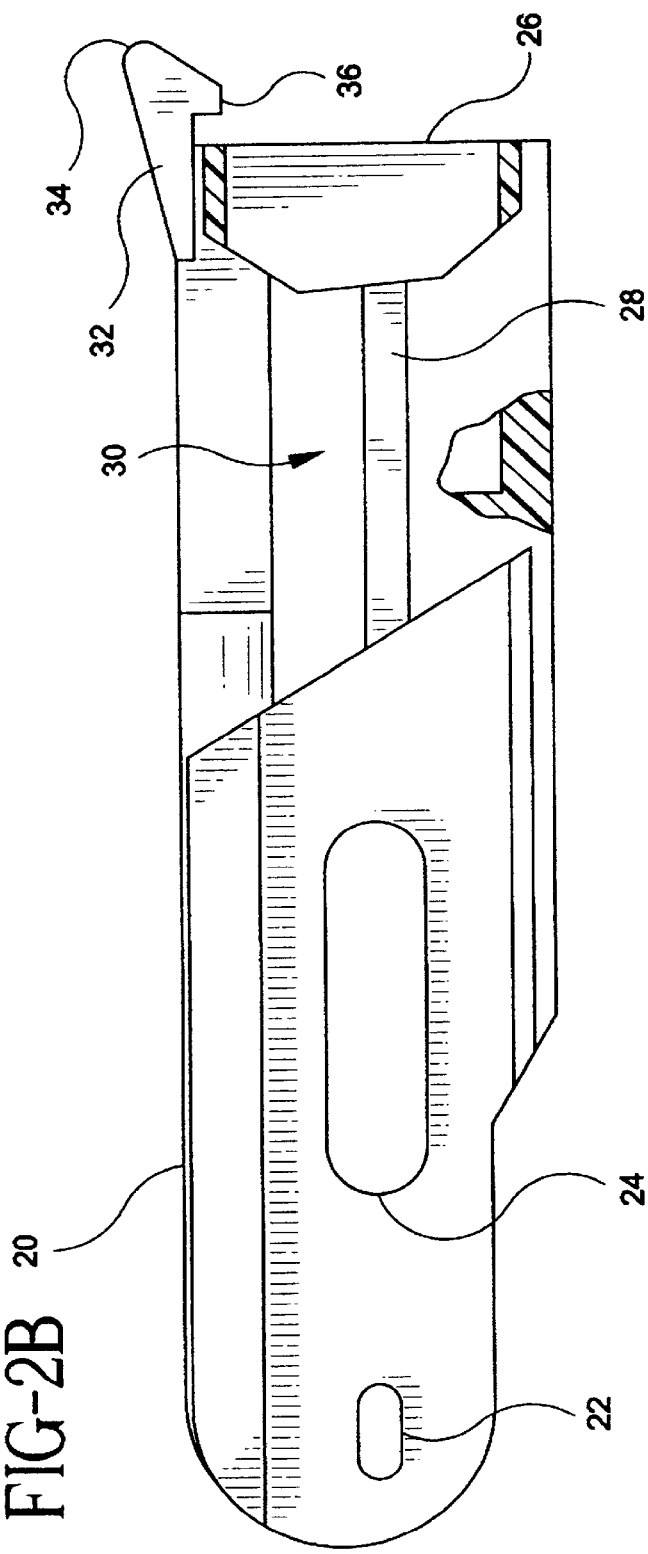
FIG. 2b is a side elevation view of the blade holder illustrating the position of the hook in the preferred embodiment and illustrating a partial section view of the attachment slot.

Turning in detail to the figures, the surgical scalpel 10 is first shown in FIG. 1 with the blade 12 secured to the blade holder 20. The scalpel 10 is gripped by the handle 50 which has a preferably contoured elongated grip portion 52. As shown in FIGS. 2a and 2b, adjacent the front end of the blade holder 20 are two tabs 22 and 24 for securing the blade 12 to the blade holder 20 by interlocking with respective openings on the blade 12. Adjacent the back end of the blade holder 20 is the attachment slot 26 shown as a female end connection. Channels 28 are positioned longitudinally on opposite sides of the blade holder 20 along a channel section 30 of the blade holder 20.

A hook 32 is cantilevered from the back end of the blade holder 20. The hook 32 can resiliently flex upwardly and downwardly to engage the handle 50. The cantilevered end of the hook 32 has an inclined aft surface 34 and a protrusion 36 which is adapted to engage a complementary shaped groove 60 on the handle 50 when the blade holder 20 mates with the handle 50.

Figure 3A:
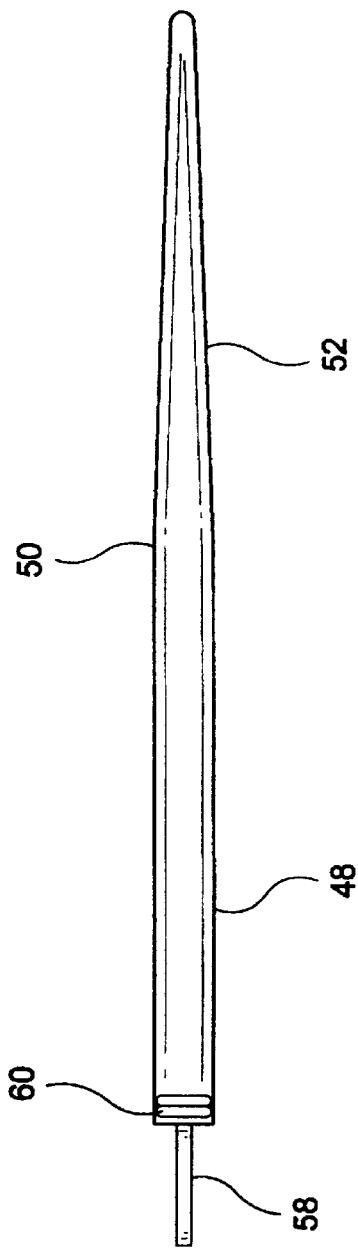
FIG. 3a is a top view of the handle shown in FIG. 1.
Figure 3B:
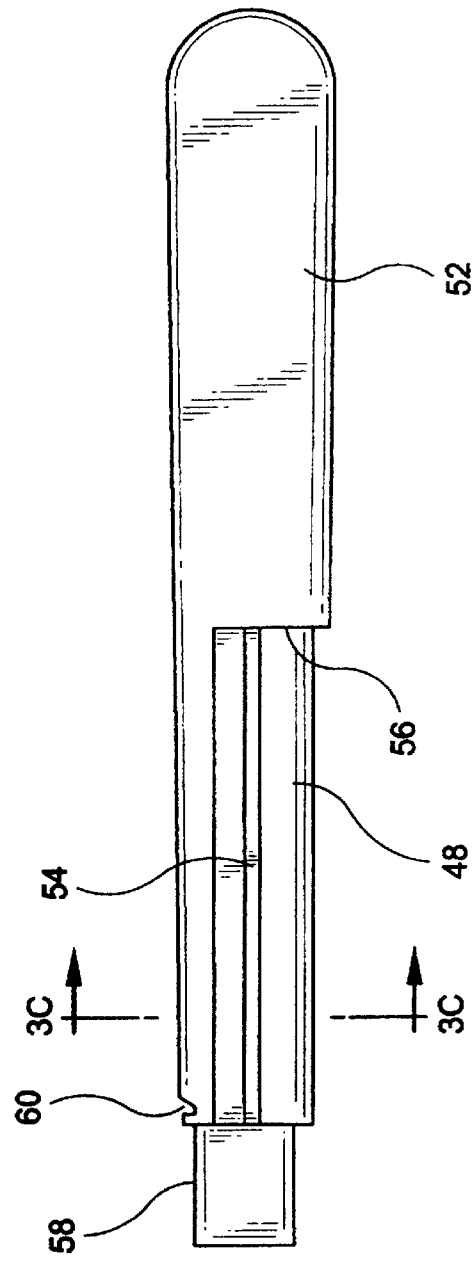
FIG. 3b is a side elevation view of the handle illustrating the groove and a male end attachment flange.

Referring now to FIGS. 3a and 3b, a pair of guide channels 54 are provided on opposite sides of the guide channel section 48 of the handle 50 in front of the grip portion 52. The guide channels 54 terminate at detents 56 where the guide channel section 48 adjoins the grip portion 52.

Figure 3D:
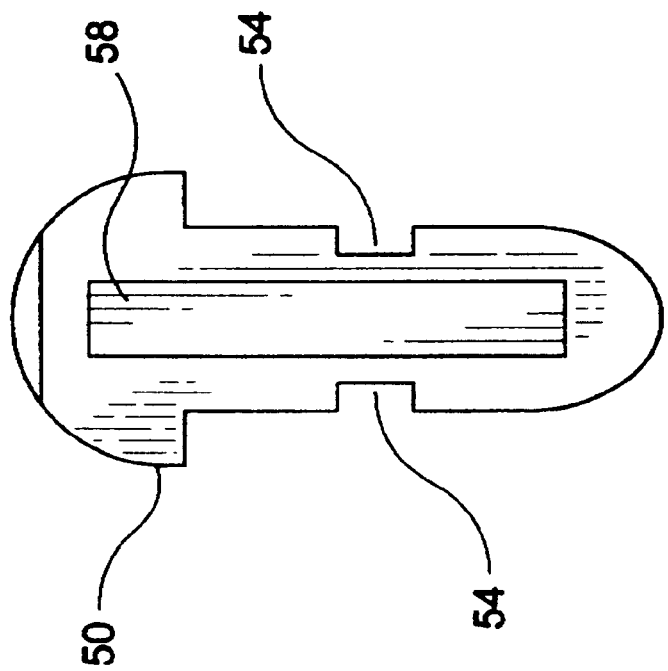
FIG. 3d is a front end view of the handle.
Figure 3C:
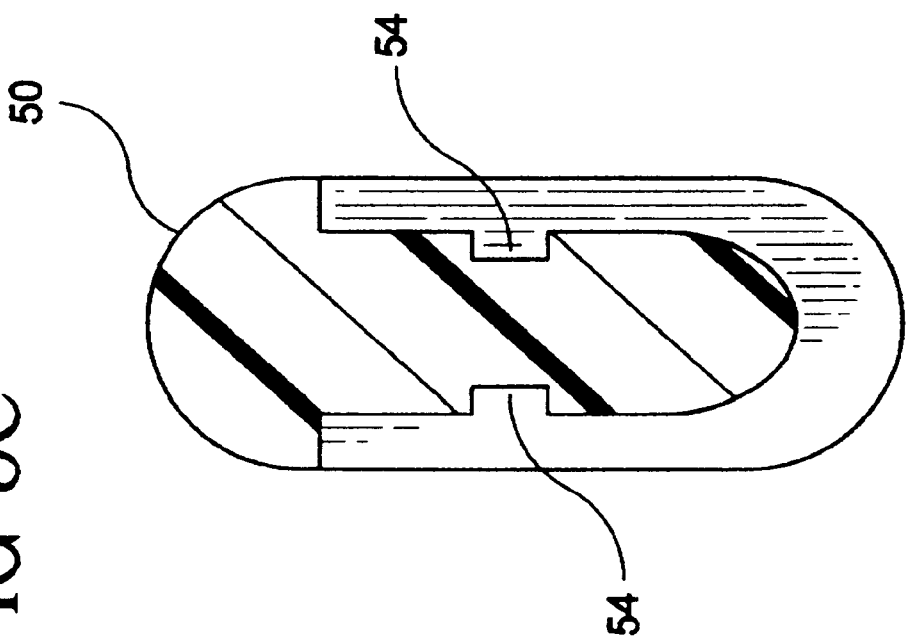
FIG. 3c is a section view taken along line 3c—3c of FIG. 3b.
Figure 4C:
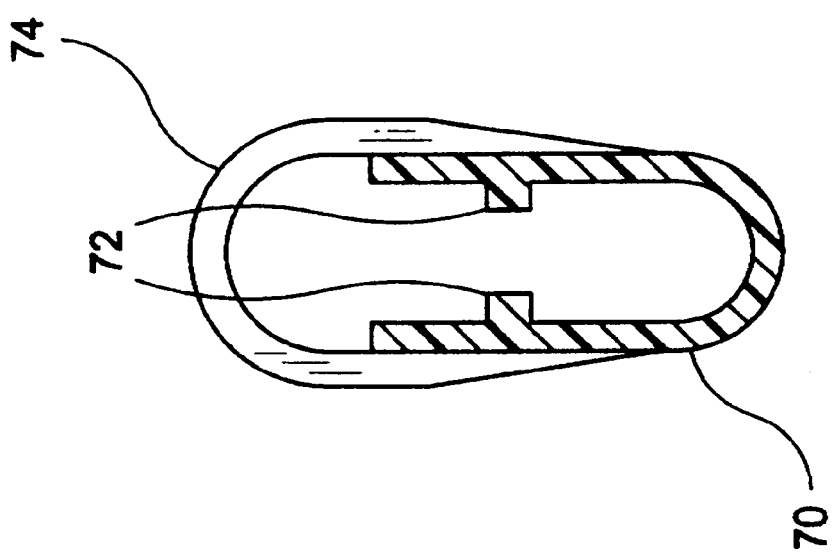
FIG. 4c is a section view of the sleeve taken along line 4c—4c of FIG. 4b.
Figure 4D:
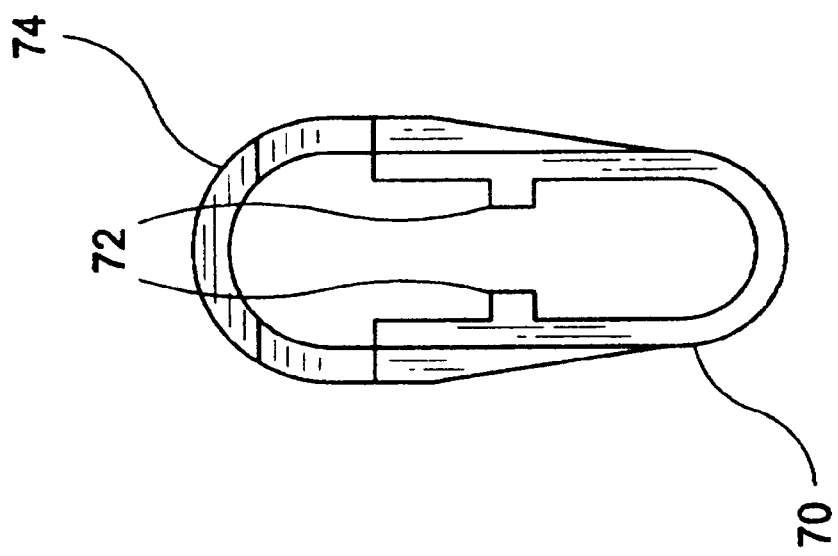
FIG. 4d is a front end view of the sleeve showing the arch.

An attachment flange 58 (shown as a male ended attachment) is joined to the front end of the guide channel section 48. As shown in FIGS. 3b and 3d, the attachment flange 58 is generally rectangular in cross section, although other configurations are possible, and is adapted to mate with the attachment slot 26 of the blade holder 20. A groove 60 at the forward end of the guide channel section 48 is shaped to mate with the hook 32.

Next referring to FIGS. 4a through 4d, the sleeve 70 is generally U-shaped in cross section having a closed bottom portion and an open upper portion. A pair of guide flanges 72 are positioned within the sleeve 70 and are adapted to engage the guide channels 54 and 28. An arch 74 at the back end of the sleeve 70 spans between the two sides of the sleeve 70. The arch 74 preferably has a radiused front surface 76.

Figure 5A:
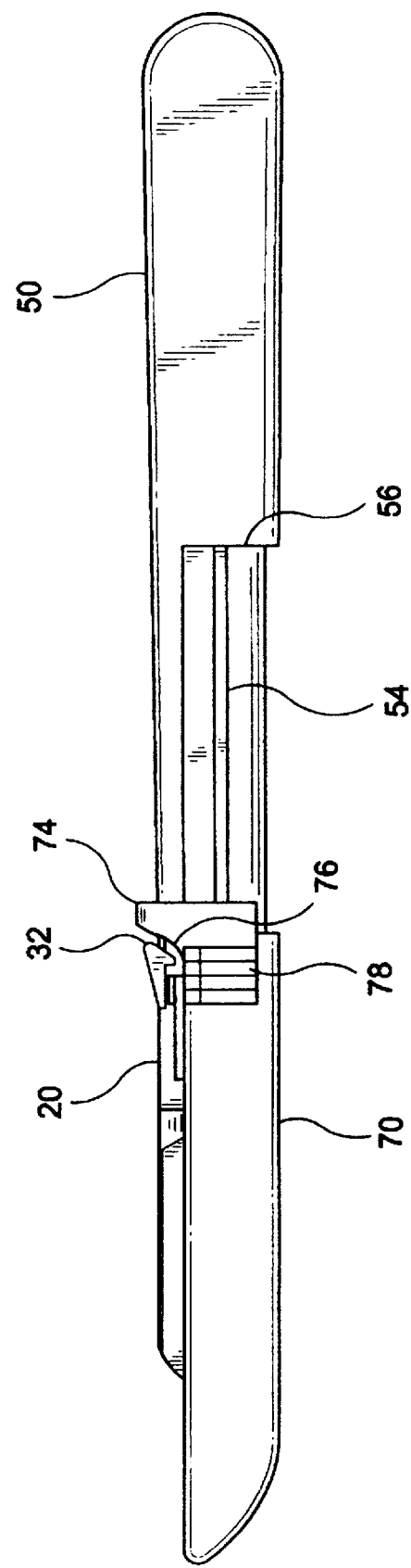
FIG. 5a is a side elevation view of the assembled scalpel with the sleeve positioned in an extended position.

The sleeve 70 preferably has a digit engaging portion 78 adjacent to the arch 74 having a series of ribs forming a thumb rest. The digit engaging portion 78 improves the surgeon's "feel" for the sleeve 70 when the sleeve 70 slides along the guide channels 28 and 54 by hand or thumb pressure. FIG. 5a shows an assembled scalpel 10 with the sleeve 70 in a forward position to cover or sheath the blade 12. The forward movement of the sleeve 70 is guided by the guide flanges 72 that travel along the guide channels 28 and 54. With the sleeve 70 moved fully forward, the radiused surface 76 contacts the hook 32 to stop additional forward movement.

Additional forward movement by the sleeve 70 toward the extended position as guided by the user's hand will cause the arch 74 to lift the hook 32 out of the groove 60 for removal of the blade holder 20 from the handle 50. This allows the sleeve 70 and blade holder 20 to be disassembled as a unit from the handle 50 while the blade 12 is sheathed by the sleeve 70, thus minimizing the risks of inadvertent cuts. The blade 12, blade holder 20 and sleeve 70 may then be disposed of. The handle may advantageously be reused.

Figure 5B:
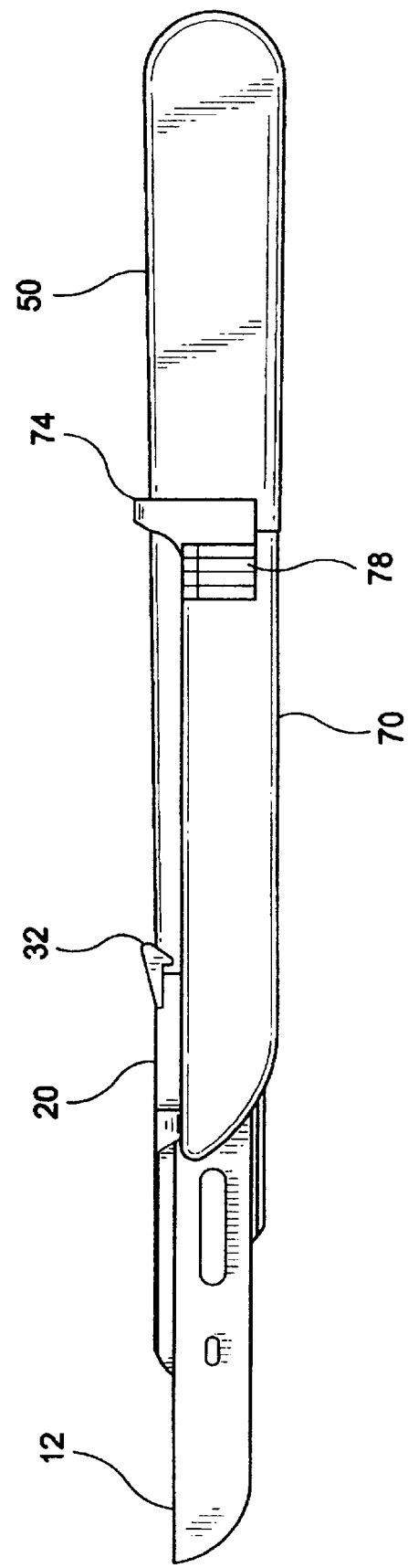
FIG. 5b is an elevation view thereof with the sleeve in a retracted position.

FIG. 5b shows the sleeve 70 moved to the fully retracted position with the back end of the sleeve 70 abutting the detents 56 to fully expose the blade 12. The user may utilize the digit engaging portion 78 on the sleeve 20 to improve fingertip control of the longitudinal front to back movement of the sleeve 70. FIG. 5c shows the sleeve 70 removed from the handle 50 (for purposes of illustration).

Figure 6:
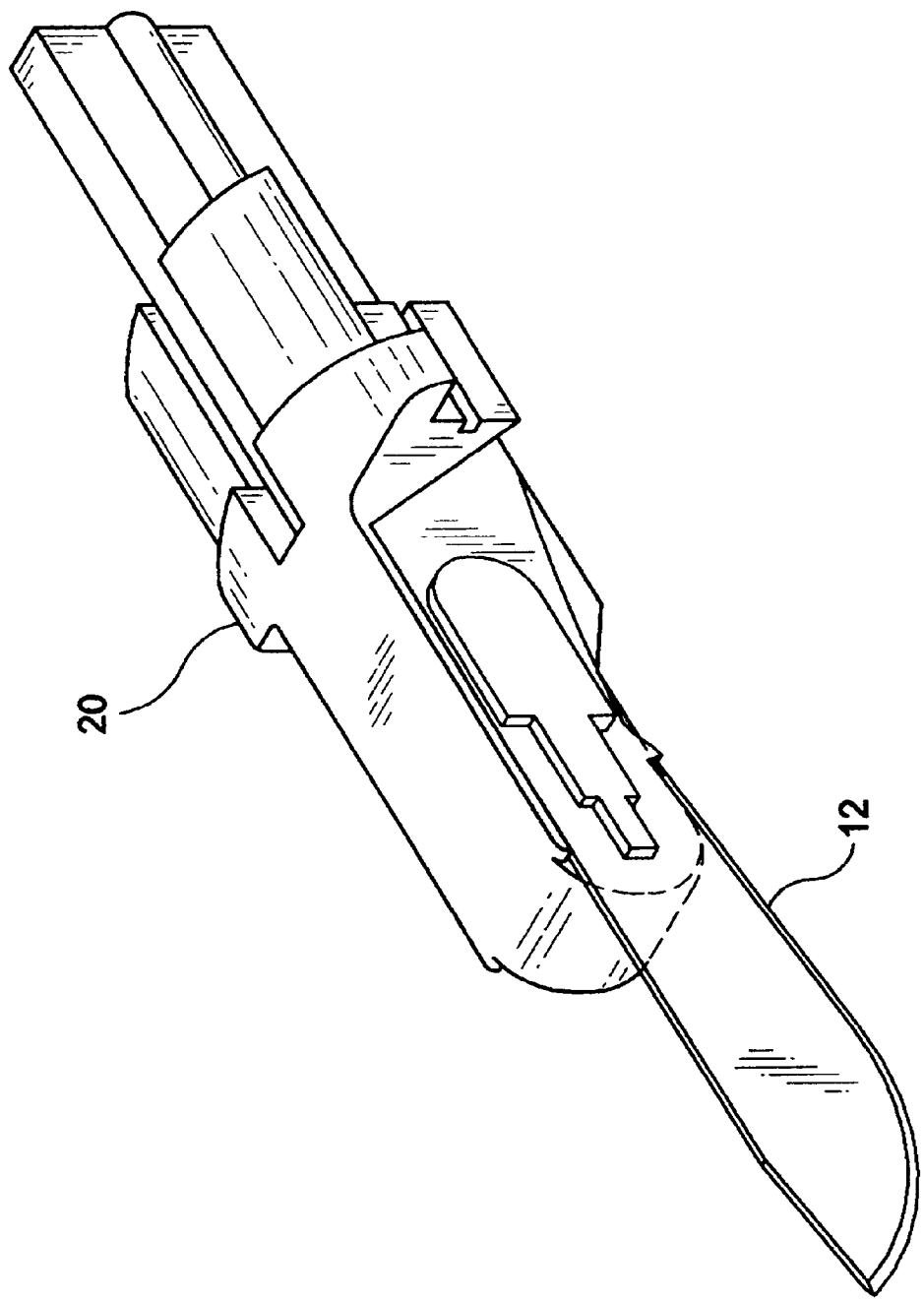
FIG. 6 shows a perspective view of an alternative embodiment of the blade holder with the blade attached.
Figure 7:
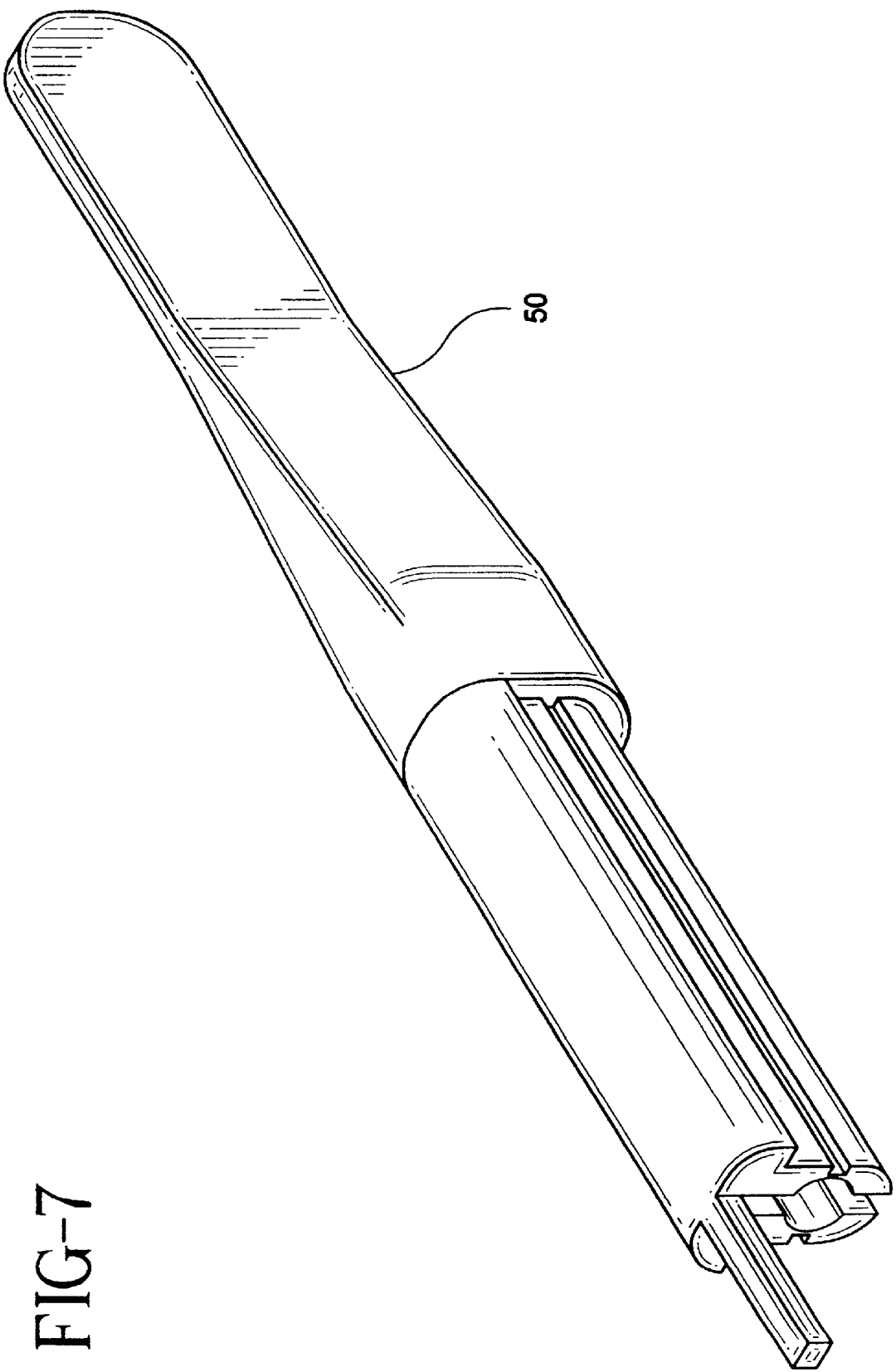
FIG. 7 is a perspective view of an alternative embodiment of the handle.
Figure 8:
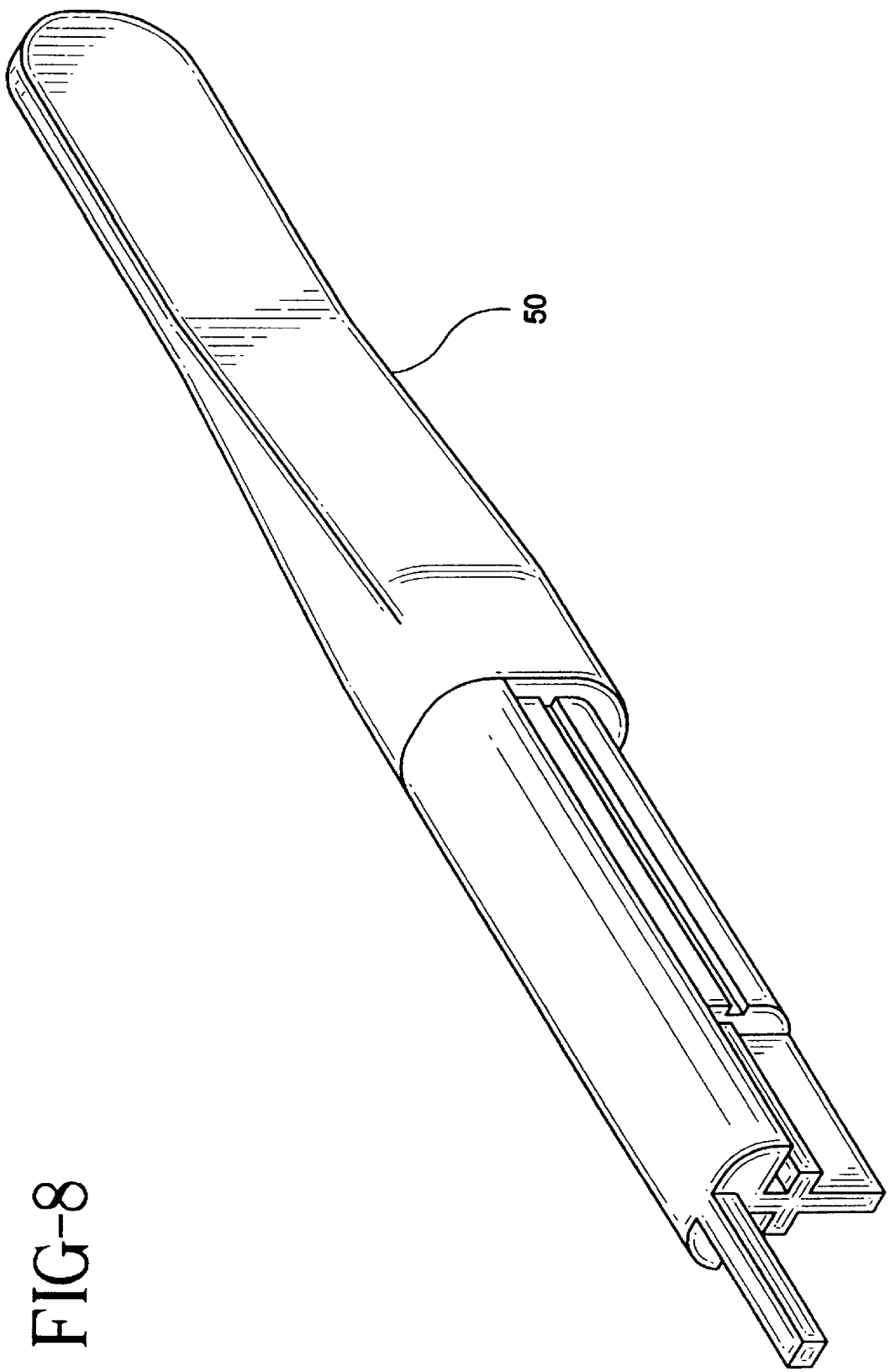
FIG. 8 is a perspective view of a second alternative embodiment of the handle.

FIG. 6 illustrates an embodiment of the blade holder 20 with both a male ended attachment and a female ended slot. FIG. 7 shows an embodiment of the handle 50 which mates with the blade holder 20 shown in FIG. 6. An alternative embodiment of the handle 50 is also shown in FIG. 8 with male ended connections. An embodiment of the blade holder 20 which mates with the handle 50 of FIG. 8 is further shown in FIG. 9 with an outline of the attached blade 12. An alternative embodiment of the sleeve 70 is shown in FIG. 10 which illustrates a stop tab 80 which may be utilized to stop forward longitudinal sliding of the sleeve 70. An inclined digit engaging portion 78 feature is illustrated and may be used to facilitate use as a thumb rest for the operating surgeon.

In an alternative embodiment 90 as shown in FIG. 11, a handle 92 has a flange 94 with vertical tabs or protrusions 96. A blade holder 98 has internal vertical slots 100 adapted to vertically slide down over the tabs 96, from above. A sleeve 102 is secured to the blade holder 98, as described above with reference to FIGS. 1–5. The sleeve 102 has a slot 104 at the back end of its lower surface. In use, the blade holder 98 is attached to the handle 92 by engaging the vertical tabs 96 into the vertical slots 100, by sliding the blade holder 98 down onto the handle 92 from above. The slot 104 in the bottom of the sleeve 102 provides sufficient clearance for the protruding vertical tabs 96.

Turning to FIG. 12, a surgical scalpel 110 has a handle 112 with a threaded stud 114 at its front end. The stud 114 threads into a threaded hole 118 at the back end of a blade holder 116. The threads on the stud 114 and in the threaded hole 118 are advantageously cut so that when the blade holder 116 bottoms out of the front end of the handle 112, the blade holder 116 will be properly vertically aligned. A sleeve 119 overlies the blade holder 116. The operation and design features of the surgical scalpels shown in FIGS. 11 and 12 are similar to the embodiment in FIGS. 1–5, except as described above.

Figure 14:
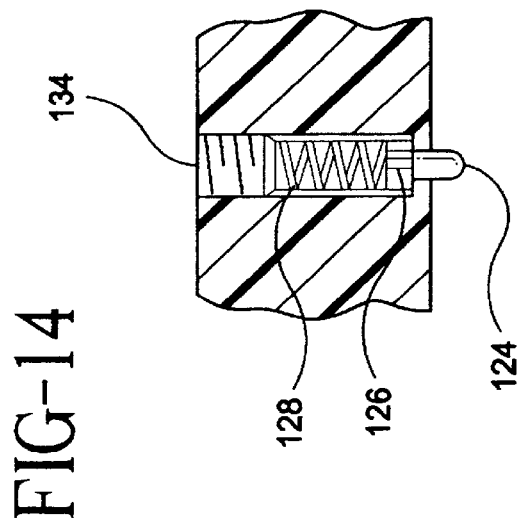
FIG. 14 is an enlarged section view of the locking button of FIG. 13.
Figure 13:
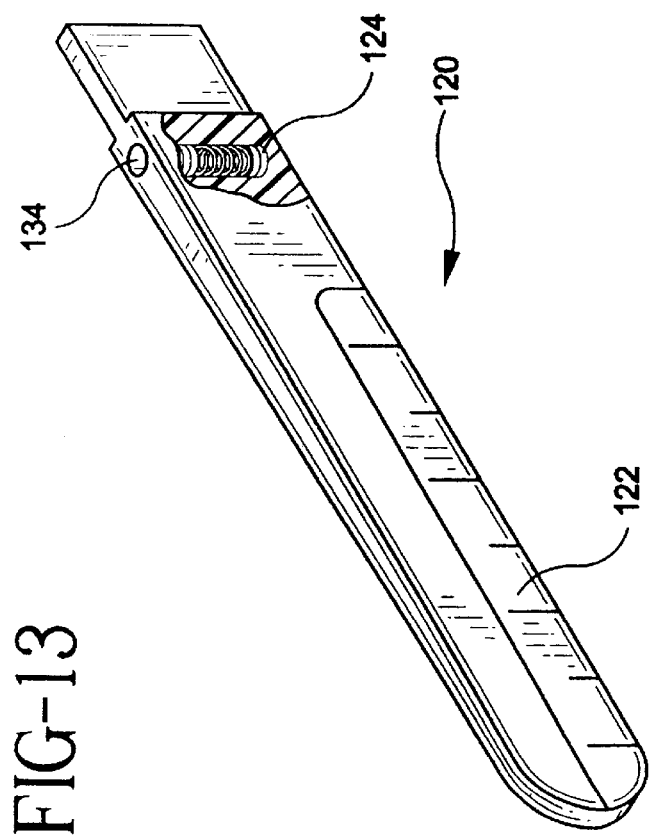
FIG. 13 is a perspective view in part section of an alternative handle embodiment having a button for locking the shield in position over the blade.
Figure 15:
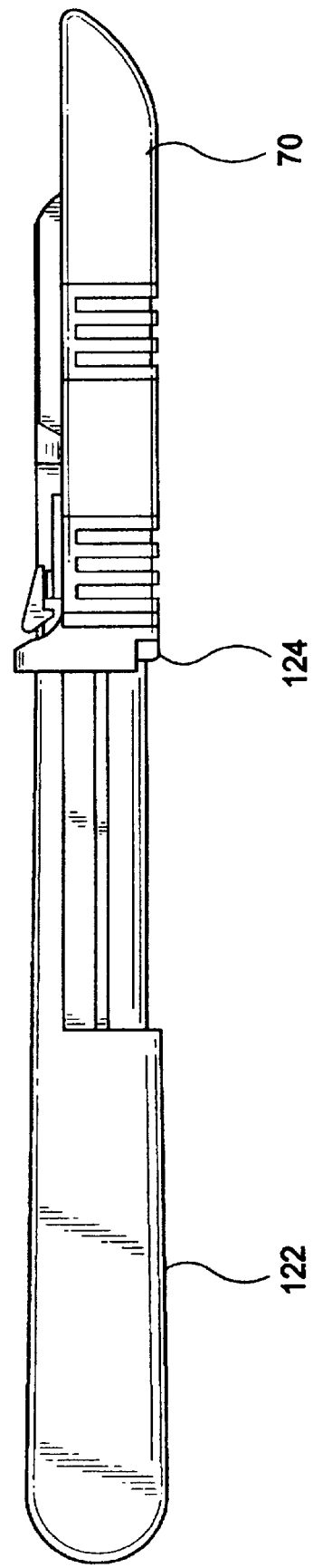
FIG. 15 is a side elevation view of the button of FIG. 14 locking the shield in its extended position.

As shown in FIG. 13, an alternative handle embodiment 122 has a locking button 124. As shown in FIG. 14, the locking button 124 has a shoulder 126 which fits within a bore 130 in the handle 122. A plug or set screw 134 at the top of the handle 122 retains a spring 128 in the bore 130, with the spring 128 biasing the locking button 124 to protrude out of the bottom surface of the handle 122. Referring to FIG. 15, with the shield 70 fully extended to cover the blade 12, the locking button 124 protrudes out of the bottom of the handle 122. The sleeve 70 can not be retracted to expose the blade, without first pushing the locking button 124 up into the bore 130. Once the locking button is pushed up into the bore, the sleeve may be retracted, with the locking button sliding in the inside lower wall or surface of the sleeve. Accordingly, the locking button 124 helps to prevent inadvertent exposing of the blade 12. The locking button feature may be used on any of the surgical scalpel embodiments described above.

While a preferred embodiment of the present invention has been shown and disclosed in the drawings and specification, alternate embodiments of the present invention would be apparent to the person of ordinary skill in the art and this application is intended to include those embodiments within the full breadth and scope of the claims. Moreover, the present invention need not include all of the features disclosed in the single embodiment but rather one or more features may be included.

What is claimed is:

1. A surgical scalpel comprising:
    a blade holder having interior vertical slots;
    a handle having vertical tabs adapted to engage the vertical slots;
    a sleeve slidable on the blade holder and the handle.

2. The scalpel of claim 1 further comprising guide channels on the blade holder and handle, and guide flanges on the sleeve engaged into the guide channels.

3. The scalpel of claim 1 further comprising a blade attached to the blade holder.

4. A surgical scalpel comprising:
    a blade holder having a back surface with a threaded opening;
    a blade fixedly attached to said blade holder
    a handle having a front surface with a threaded stud engageable into the threaded opening so that said blade projects outwardly;
    a sleeve slidable on the blade holder and the handle between a closed position wherein said blade is substantially protected from inadvertent exposure, and an open position wherein said blade is exposed for use; and wherein said blade holder having said blade fixedly attached thereto with said sleeve in said closed position is removable from said handle as a unit.

5. The scalpel of claim 4 further comprising guide channels on the blade holder and handle, and guide flanges on the sleeve engaged into the guide channels.

6. A surgical scalpel comprising:
a blade holder;
a blade fixedly attached to said blade holder;
a handle having a locking button;
means for attaching the blade holder to and detaching the blade holder from the handle;
a sleeve slidable from the blade holder, from a position wherein said blade is substantially protected from inadvertent access, onto the handle, to a position wherein said blade is exposed for use, when the locking button is pressed.

7. A surgical scalpel comprising:
a blade holder;
a blade fixedly attached to the blade holder:
a handle having a locking button;
means for attaching the blade holder to the handle so that said blade projects outwardly;
a sleeve disposed for slidable movement from the blade holder onto the handle, when the locking button is pressed between a closed position wherein said blade is substantially prevented from inadvertent exposure and a closed position an open position wherein said blade is exposed for use; and
locking means for preventing rearward movement of the sleeve.

* * * * *